US006586651B2

(12) United States Patent
Sullivan

(10) Patent No.: US 6,586,651 B2
(45) Date of Patent: *Jul. 1, 2003

(54) ADHENSIVE BANDAGE WITH SOFT, THREE-DIMENSIONAL TOY

(76) Inventor: John Patrick Sullivan, 67 Lords Highway, Weston, CT (US) 06883

( * ) Notice: Subject to any disclaimer, the term of this patent is extended or adjusted under 35 U.S.C. 154(b) by 0 days.

This patent is subject to a terminal disclaimer.

(21) Appl. No.: 09/837,509

(22) Filed: Apr. 18, 2001

(65) Prior Publication Data

US 2001/0023329 A1 Sep. 20, 2001

Related U.S. Application Data

(63) Continuation-in-part of application No. 09/430,956, filed on Nov. 1, 1999, now Pat. No. 6,255,553.

(51) Int. Cl.$^7$ ............................................. A61F 13/00
(52) U.S. Cl. ............................ 602/58; 602/41; 602/42; 602/54
(58) Field of Search ........................ 602/41–59, 60–64; D24/189; 128/877, 878, 879, 880

(56) References Cited

U.S. PATENT DOCUMENTS

| | | | |
|---|---|---|---|
| 3,736,603 A | 6/1973 | Rothman | 5/53 |
| 4,212,296 A | 7/1980 | Schaar | 128/156 |
| 4,285,338 A | 8/1981 | Lemelson | 128/155 |
| 4,334,530 A | 6/1982 | Hassell | 128/156 |
| 4,530,353 A | 7/1985 | Lauritzen | 128/156 |
| 4,832,648 A | 5/1989 | Theobald et al. | 446/72 |
| 4,913,138 A | 4/1990 | Yoshida et al. | 128/155 |
| 5,184,362 A | 2/1993 | Yager et al. | 5/490 |
| D340,988 S | 11/1993 | Arginsky | D24/189 |
| D340,989 S | 11/1993 | Arginsky | D24/189 |
| D341,888 S | 11/1993 | Arginsky | D24/189 |
| D368,526 S * | 4/1996 | Palermo | D24/189 |
| 5,533,962 A | 7/1996 | Peterman et al. | 602/54 |
| 5,542,122 A | 8/1996 | Moldovan | 2/69 |
| D394,672 S | 5/1998 | Allen et al. | D19/29 |
| 5,772,623 A | 6/1998 | Conte | 602/57 |
| 5,792,091 A | 8/1998 | Staudinger | 602/57 |
| 5,820,578 A * | 10/1998 | Johansen | 602/57 |
| 5,833,509 A | 11/1998 | Hunt | 446/73 |
| D404,135 S | 1/1999 | Dunshee | D24/189 |
| D408,540 S | 4/1999 | Dunshee et al. | D24/189 |
| 5,933,863 A | 8/1999 | Monsue | 2/21 |
| D419,678 S | 1/2000 | Gadison | D24/189 |
| D424,202 S | 5/2000 | Wilson | D24/189 |
| 6,255,553 B1 * | 7/2001 | Sullivan | 602/58 |

* cited by examiner

Primary Examiner—Kim M. Lewis
(74) Attorney, Agent, or Firm—Ware, Fressola, Van Der Sluys & Adolphson LLP

(57) ABSTRACT

An adhesive bandage having at least one soft, three-dimensional toy. In one form, a soft, three-dimensional toy figure, such as a stuffed character, animal or play object, is attached to the top surface of a flexible backing that is coated with adhesive on its skin-contacting, bottom surface and an absorbent pad is attached to the bottom surface and central portion of the flexible backing for application directly to a body wound. In another form, the toy could cover the wound directly, using either soft, three-dimensional appendages coated with adhesive or appendages made of flexible backing material coated with adhesive to attach the bandage to the skin. The bandage could also be designed so that the toy could be easily removed from the rest of the bandage components to allow for play with the toy away from the wound site.

20 Claims, 5 Drawing Sheets

ADHESIVE BANDAGE WITH SOFT, THREE-DIMENSIONAL TOY

CROSS-REFERENCE TO RELATED APPLICATIONS

This is a continuation-in-part of copending, commonly-owned U.S. patent application Ser. No. 09/430,956, filed Nov. 1, 1999, now U.S. Pat. No. 6,255,553.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of Invention

This invention relates to improvements in adhesive bandages or wound dressings and particularly to bandages having a toy component that would be attractive and entertaining for children.

2. Description of Prior Art

Adhesive bandages come in a variety of shapes and sizes. They are used to cover and protect wounds such as cuts, abrasions, punctures, and other forms of wounds inflicted on human tissue such as the skin of the arms, legs, hands, and other parts of the human body. Typically, an adhesive bandage comprises a flexible backing with an adhesive surface for attaching the bandage to the skin. Most, but not all, of these bandages have a patch of gauze or absorbent material disposed at the center of the adhesive surface. Such adhesive bandages are well-known and staple items in a first-aid kit or medicine cabinet.

In recent years, several bandage manufacturers have attempted to make bandages more attractive and entertaining, particularly to children, by the addition of colorful designs and imprinted animals and cartoon characters. Other bandages have come in fun shapes such as hearts or kissing lips. All of these bandages, though, have remained two-dimensional. These flat representations do not engage a child's imagination as readily as a three-dimensional toy representation of the character, animal, or object.

U.S. Pat. No. 4,285,338 to Lemelson (1981) describes a protective cover for a bandage and includes a raised rigid plastic shell. As one of its embodiments, the shell is a head. However, a hard cover for a bandage may not be suitable for children. Since it is hard and non-planar, it is also likely to catch on objects such as chairs and tables and prematurely fall off of the child.

U.S. Pat. No. 4,212,296 to Schaar (1980) describes a bandage with a raised protective member made of foam material. This bandage is designed only for protection and does not specify any playful figure shapes that would be entertaining for a child.

What is needed is a bandage suitable for children which includes a toy or other play shape that will capture a child's attention and enable the child's imagination to turn the distressing fact of an injury into a more positive experience.

BRIEF SUMMARY OF THE INVENTION

It is well known that children can become quite engaged with soft or plush figure toys such as teddy bears or beanbag animals. Accordingly, several objects, features and advantages of the present invention are:

(a) To provide a more attractive and entertaining adhesive bandage for children by incorporating a soft, three-dimensional toy.

(b) To provide an adhesive bandage that children are more likely to want to place over their wounds and keep over their wounds so as to speed the healing process.

(c) To provide an adhesive bandage that will make children more aware of their bandage so as to keep it from getting wet or dirty.

Other objects, features, and advantages of the present invention will become apparent from a further reading of the following summary, description, drawings and claims.

The invention comprises an adhesive bandage that incorporates at least one soft, three-dimensional toy, such as an animal, cartoon character, or the like. As used herein the term "toy" is intended to mean a play shape of the type that can capture a child's attention and provide a positive play experience. Thus, the invention will be more than a medical patch to protect a wound. It will also have a distinct toy element intended for play and amusement.

The toy can be a figure or plurality of figures generally made of soft materials similar to those of stuffed or bean-bag animals, or may be made of other soft materials, without a shell-and-stuffing configuration, such as squeezeable foam, yarn, bunched-up material (e.g., felt, wool, socks, cheese-cloth and the like), pom-poms, padding, cotton, etc. Upon application of the bandage, the toy is raised relative to the skin surface, thereby providing a three-dimensional effect.

DETAILED DESCRIPTION OF THE INVENTION

Figure 1:
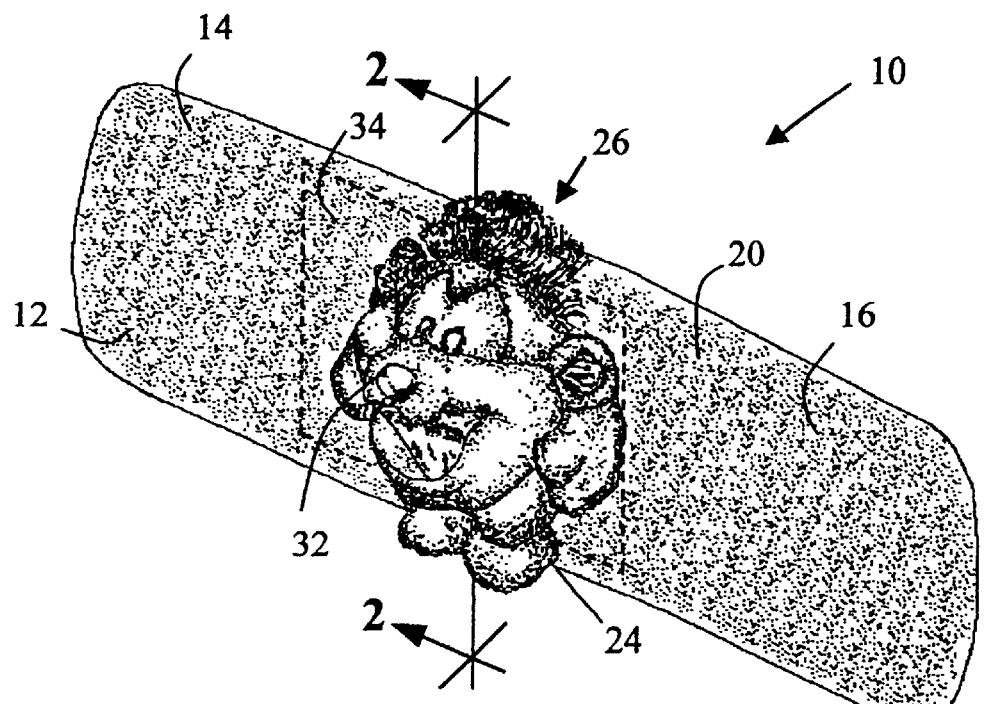
FIG. 1 is a perspective view of an adhesive bandage incorporating a soft, three-dimensional toy in the form of a cartoon character.
Figure 2:
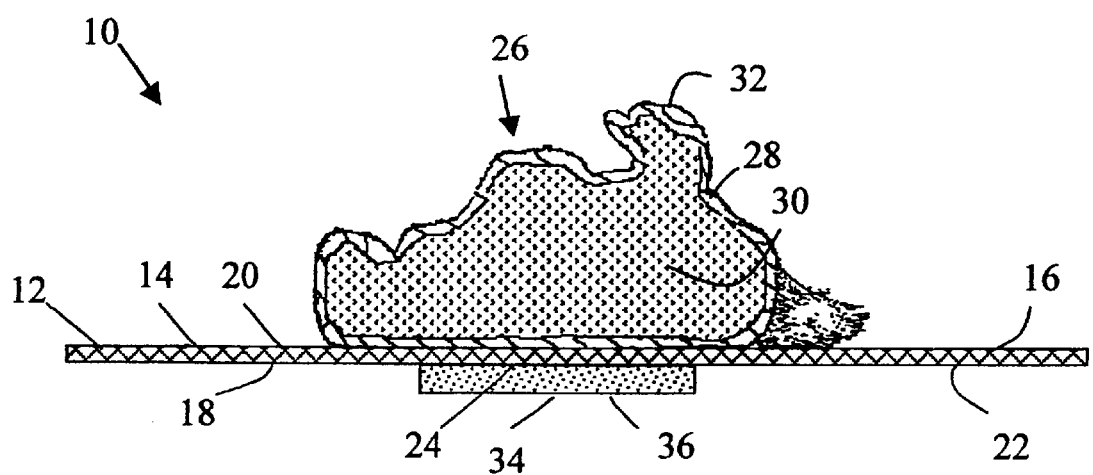
FIG. 2 is a side view in cross section of the bandage of FIG. 1.

A typical embodiment of the present invention is illustrated in FIG. 1 and FIG. 2. An adhesive bandage 10 is shown that includes a flexible backing 12, such as a strip of plastic material or woven or non-woven fabric or the like capable of receiving and retaining adhesive of the type normally employed for adhesive bandages. Backing 12 could be made of a material that is breathable, gas-permeable, and/or hydrophobic. The backing 12 could also contain one or more designs and colors and could also be made to look translucent, transparent, or opaque. These materials, their dimensions, modifications, etc., are well known in the industry.

For this embodiment, the backing 12 is in the shape of a strip having end portions 14 and 16, extending from a central portion 24. A skin-contacting or bottom surface 18 of the end portions 14 and 16 is coated with an adhesive 22 for attaching bandage 10 to the skin. Generally disposed at the central portion 24 of the bottom surface 18 of the flexible backing 12 may be an absorbent pad 34, made of gauze, cotton, or some other absorbent material, that is meant for direct contact with a body wound and therefore void of adhesive on a wound-facing surface 36. A three-dimensional toy FIG. 26 is adhesively bonded or affixed above a top surface 20 of the backing 12 in any manner effective to provide necessary physical integrity. The toy in this embodiment is a soft, three-dimensional FIG. 26 of a type that will capture a child's attention and enable the child's imagination to turn the distressing fact of an injury into a more positive experience.

The toy FIG. 26 is a stuffed cartoon character in this embodiment, though the toy FIG. 26 could take the form of any soft, three-dimensional toy figure such as an animal or entertaining toy object. The toy FIG. 26 of this embodiment comprises a soft, three-dimensional toy shell 28 and filling or stuffing 30 to provide the three-dimensional effect. Stuffing 30 is a polyester stuffing used to stuff conventional toy animals, characters, or objects. However, one skilled in the art will find it apparent that stuffing 30 could be beads, beans, fiberfill, or any conventional natural or synthetic type of stuffing used to stuff toy animals, characters, or objects. One skilled in the art would further understand that shell 28 could be created from a variety of materials used to create the shells of soft or plush three-dimensional stuffed animals, characters, or objects. The toy FIG. 26 could also not have a shell-and-stuffing configuration, but rather be made into a three-dimensional animal, character, or object using yarn, bunched-up fabric, squeezable foam, or other soft materials as described above and otherwise.

Toy FIG. 26 may also include simulated features 32 such as mock eyes, nose or other objects which could be made from hard materials, such as a rigid plastic resin, without jeopardizing the overall soft feel of the toy FIG. 26. When the bandage 10 is applied, the absorbent pad 34 is positioned over the body wound, the bottom surfaces 18 of the end portions 14 and 16 are adhered to the skin, and the toy FIG. 26 is raised relative to the skin surface.

Figure 3:
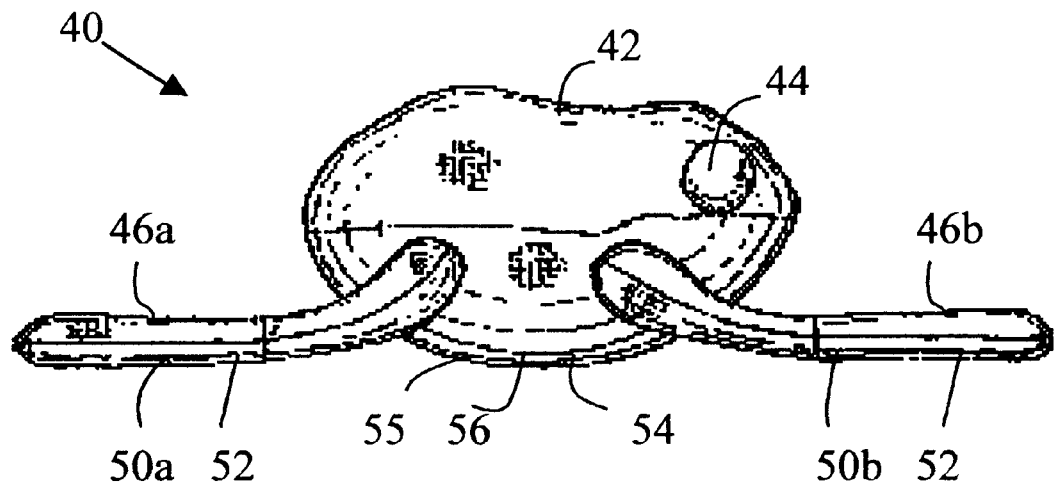
FIG. 3 is a side view of an alternate embodiment of the invention with no flexible backing.
Figure 4:
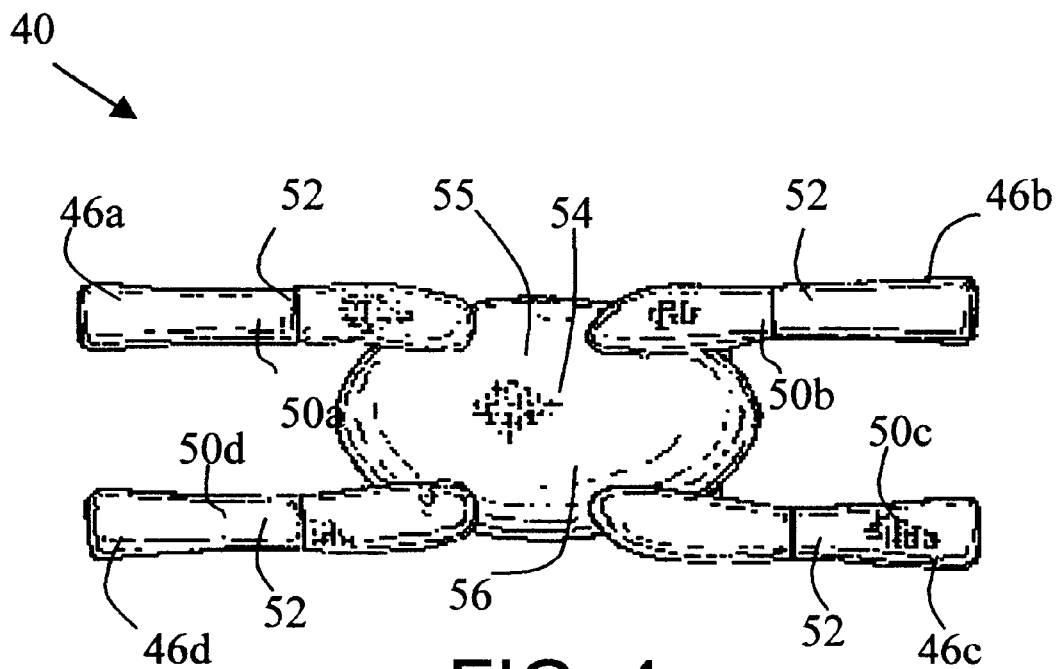
FIG. 4 is a bottom view of FIG. 3.

An additional embodiment of the present invention is shown in FIG. 3 and FIG. 4. In this embodiment, no flexible backing material and no absorbent pad is used. Rather, an adhesive bandage 40 comprises a soft, three-dimensional toy FIG. 42 with a plurality of soft, three-dimensional appendages 46a, 46b, 46c, 46d extending peripherally from the toy FIG. 42. The appendages 46a, 46b, 46c, 46d can be made of the same materials as the toy FIG. 42 or other materials conventionally used to create soft, three-dimensional animals, characters, or objects as discussed previously. The appendages 46a, 46b, 46c, 46d have adhesive 52 coating their bottom surfaces 50a, 50b, 50c, 50d respectively for attaching bandage 40 to the skin. On a bottom or skin-contacting side 56 of toy FIG. 42, located at a central portion 55 of bandage 40, is an adhesive-free area 54 which is left void of adhesive so as not to stick to the body wound on which it is placed. In this embodiment, the material of which the skin-contacting side 56 of toy FIG. 42 is made serves the same purpose as the absorbent pad of the previous embodiment. The toy FIG. 42 may also include a simulated feature 44, such as mock eyes, nose, or other object, which in this embodiment is made of the same material as toy FIG. 42, though the feature 44 can be made from a variety of conventional materials, hard or soft.

Figure 5:
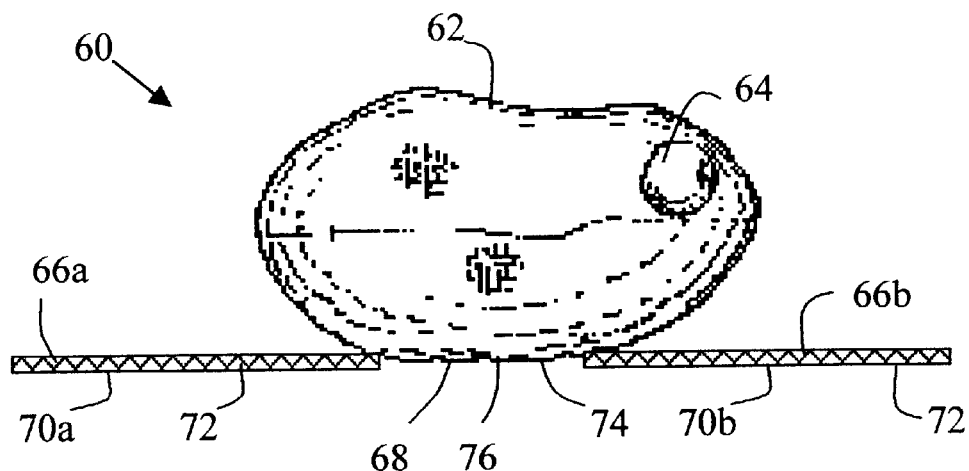
FIG. 5 is a side view of an alternate embodiment of the invention wherein the toy figure has a plurality of appendages made of flexible backing material.
Figure 6:
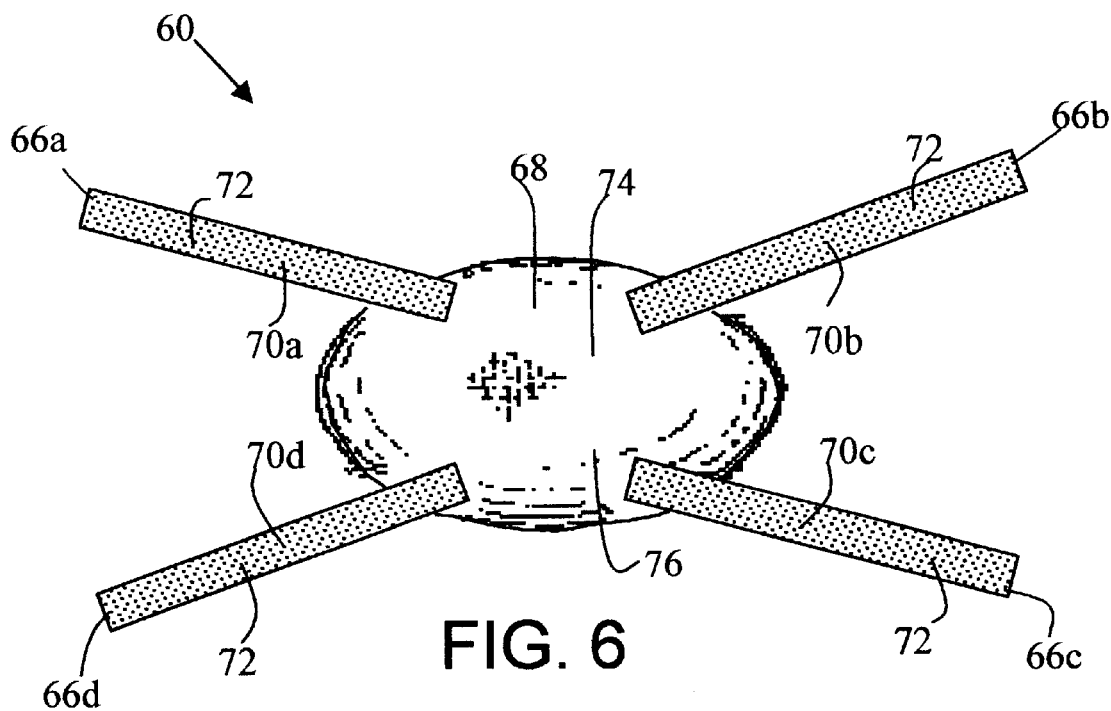
FIG. 6 is a bottom view of FIG. 5.

Another embodiment of the present invention is shown in FIG. 5 and FIG. 6. In this embodiment, an adhesive bandage 60 consists of a soft, three-dimensional toy FIG. 62 with simulated feature 64 and a plurality of appendages 66a, 66b, 66c, 66d extending peripherally from the toy FIG. 62. These appendages 66a, 66b, 66c, 66d are made of similar flexible backing material as shown in FIG. 1 and FIG. 2. The appendages 66a, 66b, 66c, 66d have bottom surfaces 70a, 70b, 70c, 70d to which is applied an adhesive 72 for attaching the bandage 60 to the skin. As in the previous embodiment, bandage 60 has an adhesive-free area 74, which is located at a central portion 68 of bandage 60, on a bottom or skin-contacting side 76 of toy FIG. 62 to allow direct contact with a body wound without sticking to the body wound. The appendages 66a, 66b, 66c, 66d are adhesively bonded or attached in any other conventional way to the skin-contacting side 76 of toy FIG. 62 without overlapping the adhesive-free area 74.

Figure 7:
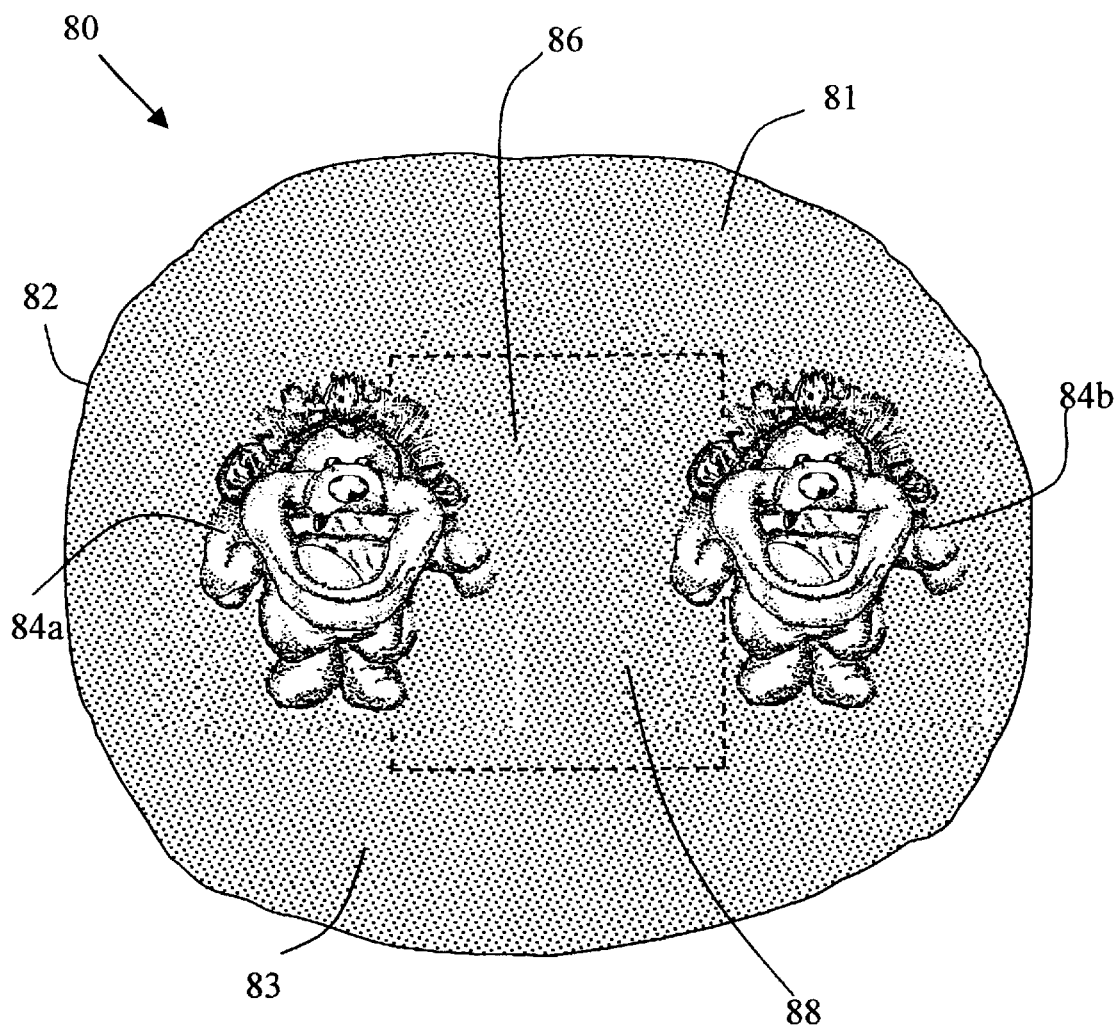
FIG. 7 is an alternate embodiment of the invention incorporating a plurality of soft, three-dimensional toy figures.

FIG. 7 shows another embodiment of the invention that includes more than one soft, three-dimensional toy figure. An adhesive bandage 80 has a flexible backing 81 in the general shape of a circle, which illustrates that the scope of this invention can cover any type of backing or bandage shape including, but not limited to, rectangular, strip, butterfly, and irregular shapes. Bandage 80 has two soft, three-dimensional toy FIGS. 84a and 84b located toward the outside edge 82 and on a top surface 83 of backing 81. On the skin-contacting, bottom surface (not shown) of the backing 81, at a central portion 86 of bandage 80 is an absorbent pad 88 for application directly to a body wound.

Figure 8:
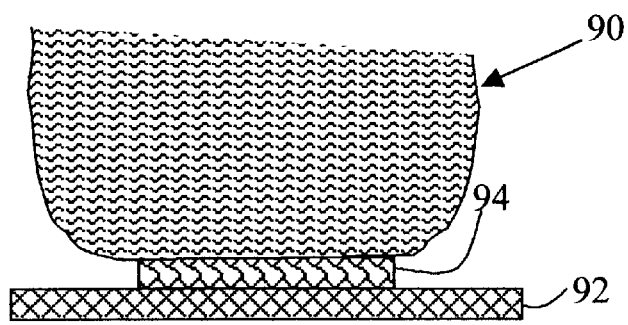
FIG. 8 is a partial side view showing a soft, three-dimensional toy figure, a flexible backing for an adhesive bandage, and means for joining them together.
Figure 9:
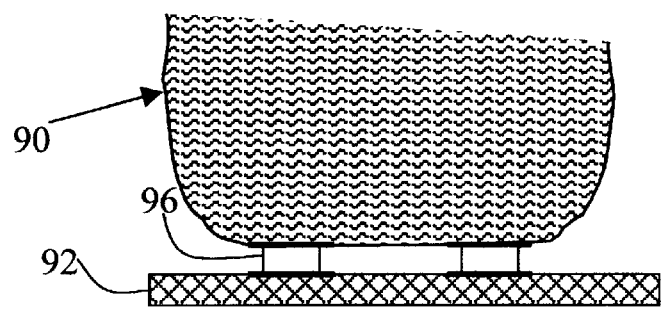
FIG. 9 is a partial side view showing a soft, three-dimensional toy figure, flexible backing for an adhesive bandage, and means for joining them together.
Figure 10:
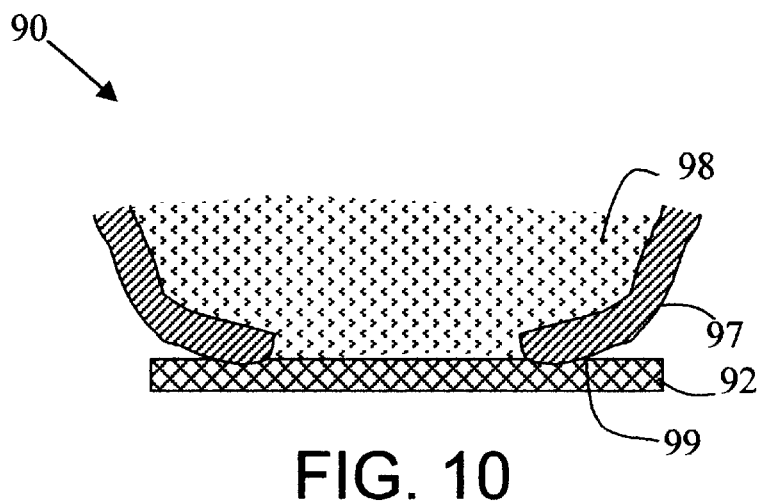
FIG. 10 is a partial side view showing a cross-section of a soft, three-dimensional toy figure, a flexible backing for an adhesive bandage, and means for joining them together.

FIG. 8, FIG. 9, and FIG. 10 show three alternate embodiments of connecting a soft, three-dimensional toy 90 to flexible backing 92. In FIG. 8 and FIG. 9, toy 90 is removably affixed to flexible backing 92. In FIG. 8, there is a VELCRO® brand feature 94 of hooks and loops, manufactured by Velcro Industries, B. V., for effecting the affixation. In FIG. 9 there are press buttons 96. The methods to removably affix the toy 90 from the backing 92, though, can be accomplished in many other ways, including, but not limited to, regular buttons, a weak adhesive, safety pins, T-pins, other pins, button-slit configuration, clips, static cling, elastic band around finger or other body part, snaps, hook-and-eye connectors, snap-fit connectors, ribbons, ties, double-sided tape, and the like. FIG. 10 illustrates how a soft, 3D toy shell 97 does not have to completely encase a filling or stuffing 98. Rather stuffing 98 is bordered in part by shell 97 and by backing 92. Shell 97 is attached adhesively or through other conventional means at interengaging position 99 on backing 92.

Thus there is provided in accordance with the invention a novel and highly effective bandage that accomplishes the objects of the invention set out above. It is intended that all matter contained in the specifications, descriptions and discussions above shall be interpreted as illustrative and not in a limiting sense. Many modifications of the presently preferred embodiments of the invention disclosed above will readily occur to those skilled in the art. For example, instead of the appendages of FIG. 5 and FIG. 6 being attached to the soft, three-dimensional toy figure, they could be attached to the sides of an absorbent pad with the toy figure attached to the top of the absorbent pad. The appendages could not be appendages at all but rather one continuous apron around the toy figure or any of a variety of shapes intended to attach the bandage to the skin. The invention could employ these or any of a variety of combinations of attachments, shapes and materials using similar components to those described. In addition, located at the previously described central portion of the bandage meant for direct contact with a body wound, there could be an area on the bottom surface of a flexible backing that is void of adhesive, rather than using an absorbent pad or having the bottom of the toy figure be adhesive-free. Accordingly, the scope of the invention should be determined not by the embodiments illustrated, but by the appended claims and their legal equivalents.

I claim:

1. An adhesive bandage comprising:
   means for attaching said bandage to the skin,
   at least one soft, three-dimensional toy figure affixed to said means for attaching, and
   a substantially central portion for application directly to a body wound.

2. The adhesive bandage of claim 1 wherein said soft, three-dimensional toy is a stuffed animal.

3. The adhesive bandage of claim 2 wherein said stuffed animal is a beanbag animal.

4. The adhesive bandage of claim 1 wherein said soft, three-dimensional toy is a stuffed character.

5. The adhesive bandage of claim 4 wherein said stuffed character is a beanbag character.

6. The adhesive bandage of claim 1 wherein said soft, three-dimensional toy is a stuffed object.

7. The adhesive bandage of claim 6 wherein said stuffed object is a beanbag object.

8. The adhesive bandage of claim 1 wherein said soft, three-dimensional toy further comprises at least one simulated feature made of a hard material.

9. The adhesive bandage of claim 1 wherein there is more than one said soft, three-dimensional toy and said toys are not all identical to each other.

10. The adhesive bandage of claim 1 wherein said soft, three-dimensional toy is made of a squeezable foam material.

11. The adhesive bandage of claim 1 wherein said substantially central portion contains an absorbent pad.

12. The adhesive bandage of claim 1 wherein said substantially central portion contains an area on a skin-contacting surface of said soft, three-dimensional toy that is void of adhesive.

13. The adhesive bandage of claim 1 wherein said soft, three-dimensional toy is removably affixed to said means for attaching.

14. The adhesive bandage of claim 1 wherein said means for attaching comprises a flexible backing coated at least partially on one side with adhesive.

15. The adhesive bandage of claim 1 wherein said means for attaching comprises a plurality of soft, three-dimensional appendages integral with said soft, three-dimensional toy, and said plurality of soft, three-dimensional appendages are coated at least partially on one side with adhesive.

16. The adhesive bandage of claim 1 wherein said means for attaching comprises a plurality of appendages made of flexible backing material and affixed to said soft, three-dimensional toy, with said plurality of appendages being coated at least partially on one side with adhesive.

17. The adhesive bandage of claim 1 wherein said means for attaching comprises a flexible backing coated at least partially on one side with adhesive, and wherein said soft, three-dimensional toy is a stuffed toy comprising a shell and a stuffing material, with said stuffing material being encased partially by said shell and partially by said flexible backing.

18. An adhesive bandage comprising:
    flexible backing coated at least partially on one side with adhesive for attaching said bandage to the skin,
    at least one soft, three-dimensional toy figure affixed to said flexible backing, and
    a substantially central portion for application directly to a body wound.

19. A method of forming an adhesive bandage comprising:
    providing a means for attaching said bandage to the skin,
    affixing at least one soft, three-dimensional toy figure to said means for attaching,
    providing a substantially central portion for application directly to a body wound.

20. An adhesive bandage comprising:
    means for attaching said bandage to the skin,
    a substantially central portion for application directly to a body wound, said substantially central portion containing an absorbent pad which is affixed to said means for attaching, and
    at least one soft, three-dimensional toy figure affixed to said absorbent pad.

* * * * *